US00PP11454P

United States Patent [19]

van Rijn

[11] Patent Number: Plant 11,454

[45] Date of Patent: Jul. 18, 2000

[54] ANTHURIUM PLANT NAMED 'CYNTHIA'

[75] Inventor: Leonardus van Rijn, Schipluiden, Netherlands

[73] Assignee: Rijnplant B.V., Schipluiden, Netherlands

[21] Appl. No.: 09/177,291

[22] Filed: Oct. 22, 1998

[51] Int. Cl.[7] ..... A01H 5/00

[52] U.S. Cl. ..... Plt./366

[58] Field of Search ..... Plt./365, 366

[56] References Cited

U.S. PATENT DOCUMENTS

P.P. 9,088 3/1995 van Rosmalen ..... Plt./366

P.P. 9,703 11/1996 Rotolante ..... Plt./366

*Primary Examiner*—Howard J. Locker
*Assistant Examiner*—Kent L. Bell
*Attorney, Agent, or Firm*—C. A. Whealy

[57] ABSTRACT

A distinct cultivar of Anthurium plant named 'Cynthia', characterized by its compact, upright, outwardly arching and very freely clumping growth habit; rapid growth rate and high vigor; very dark green leaves that are ovate in shape; numerous inflorescences that are positioned upright and above the foliage on strong and erect scapes; durable white spathes and white spadices; year-round continuous flowering; and good post-production longevity.

2 Drawing Sheets

BACKGROUND OF THE INVENTION

The present invention relates to a new and distinct cultivar of Anthurium plant, botanically known as *Anthurium andreanum*, and hereinafter referred to by the cultivar name 'Cynthia'.

The new Anthurium is a product of a planned breeding program conducted by the Inventor in Schipluiden, The Netherlands. The objective of the program is to create new compact Anthurium cultivars that have a freely clumping growth habit, strong rooting system, strong plant growth, attractive spathe color, numerous inflorescences and leaves, and good post-production longevity.

The new Anthurium originated from a self-pollination by the Inventor on Mar. 21, 1994 of the Inventor's proprietary *Anthurium andreanum* selection code number 93-9. The cultivar 'Cynthia' was discovered and selected by the Inventor as a plant within the progeny of the stated cross in a controlled environment in Schipluiden, The Netherlands in the December, 1995.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Cynthia'. These characteristics in combination distinguish 'Cynthia' as a new and distinct cultivar:

1. Compact, upright, outwardly arching and very freely clumping growth habit.

2. Rapid growth rate and vigorous.

3. Very dark green leaves that are ovate in shape.

4. Numerous inflorescences that are positioned upright and above the foliage on strong and erect scapes.

5. Durable white spathes and white spadices.

6. Year-round continuous flowering.

7. Good post-production longevity.

The new Anthurium can be compared to the parent, the Inventor's proprietary selection code number 93-9. In side-by-side comparisons conducted by the Inventor in Schipluiden, The Netherlands, plants of the new Anthurium differ from plants of selection code number 93-9 in the following characteristics:

1. Plants of the new Anthurium are have darker green and rougher leaves than plants of the selection code number 93-9.

2. Plants of the new Anthurium have rougher spathes than plants of the selection code number 93-9.

3. Plants of the new Anthurium have white spathes whereas plants of the selection code number 93- 9 have pink spathes.

The new Anthurium can be compared to the nonpatented Anthurium cultivar 'Desiree'. In side-by-side comparisons conducted by the Inventor in Schipluiden, The Netherlands, plants of the new Anthurium differ from plants of the cultivar 'Desiree' in the following characteristics:

1. Plants of the new Anthurium are more compact than plants of the cultivar 'Desiree'.

2. Plants of the new Anthurium are more freely clumping than plants of the cultivar 'Desiree'.

3. Plants of the new Anthurium have much darker green leaves than plants of the cultivar 'Desiree'.

4. Plants of the new Anthurium have stronger roots than plants of the cultivar 'Desiree'.

5. Plants of the new Anthurium and the cultivar 'Desiree' differ in spathe shape.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type.

The photograph on the first sheet comprises a top perspective view of a typical potted plant of the cultivar 'Cynthia'.

The photograph on the second sheet comprises a close-up view of a typical spathe and spadix of the cultivar 'Cynthia'. Leaf, spathe and spadix colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in Schipluiden, The Netherlands, in a glass greenhouse with an average day temperature of 25° C. and an average night temperature of 19° C.

Botanical classification: *Anthurium andreanum* cultivar 'Cynthia'.

Parentage:

*Female parent.*—Inventor's proprietary *Anthurium andreanum* selection code number 93-9.

*Male parent.*—Inventor's proprietary *Anthurium andreanum* selection code number 93-9.

Propagation:

*Method.*—Typically by tissue culture.

*Time to initiate roots.*—About 70 to 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Erect when young, becoming outwardly arching as leaves develop. Compact, freely clumping, bushy and dense. Appropriate for 17 to 35-cm containers.

*Plant height.*—About 42.5 cm from soil level to apex of spathes.

*Plant vigor.*—Vigorous.

*Growth rate.*—Rapid.

*Crop time.*—About 10 months are usually required from planting of young plants to finished plants in 17-cm container.

*Foliage description.*—Quantity: Usually about 20 leaves per container. Length: About 27 cm. Width: About 18.5 cm. Shape: Ovate. Apex: Apiculate to cuspidate. Base: Auriculate to cordate; lobes not overlapping. Margin: Entire, undulate. Texture: Smooth, glabrous, leathery. Color: Young leaves, upper surface: Darker than 144A. Young leaves, lower surface: Darker than 144A. Mature leaves, upper surface: Between 139A and 147A. Mature leaves, lower surface: Darker than 144A. Petiole: Length: About 28.5 cm. Color: 144A. Geniculum length: About 2.5 cm.

Inflorescence description:

*Inflorescence arrangement.*—Spathe with spadix held above the foliage. Flowering structures arise from leaf axils. Freely flowering; continuous flowering year-round; typically four to eight inflorescences per plant. Not fragrant.

*Inflorescence longevity.*—Inflorescences last about six weeks under winter conditions and up to three months under summer conditions; persistent.

*Flowers.*—Quantity per spadix: Numerous, about 150. Shape: Rounded. Diameter: About 1 mm, maximum.

*Spathe.*—Length: About 9 cm. Width: About 8.25 cm. Height above foliage: About 3 cm. Shape: Deltoid. Apex: Apiculate to mucronate. Base: Auriculate to cordate; lobes not overlapping. Margin: Entire. Texture: Leathery, glabrous, very slight blistering, shiny. Color: When opening: 158B. Front surface: 155B. Back surface: 155B. After senescence: 155B.

*Spadix.*—Length: About 5.5 cm. Diameter: About 8 mm. Shape: Columnar. Cross section: Rounded. Longitudinal axis: Weakly recurved. Color: Immature: Close to 146A. Mature: Base: Creamy white, 159B. Mid-section: Close to 159B. Apex: 21C. After senescence: 159B.

*Scape.*—Length: About 31.5 cm. Aspect: Strong and erect. Color: 144A.

*Reproductive organs.*—Androecium: Pollen color: Creamy white, 158D. Gynoecium: Stigma shape: Ovoid.

Disease resistance: Plants of the new Anthurium have not been shown to be resistant to diseases common to Anthurium.

Seed development: Seed development on plants of the new Anthurium has not been observed.

It is claimed:

1. A new and distinct cultivar of Anthurium plant named 'Cynthia', as illustrated and described.

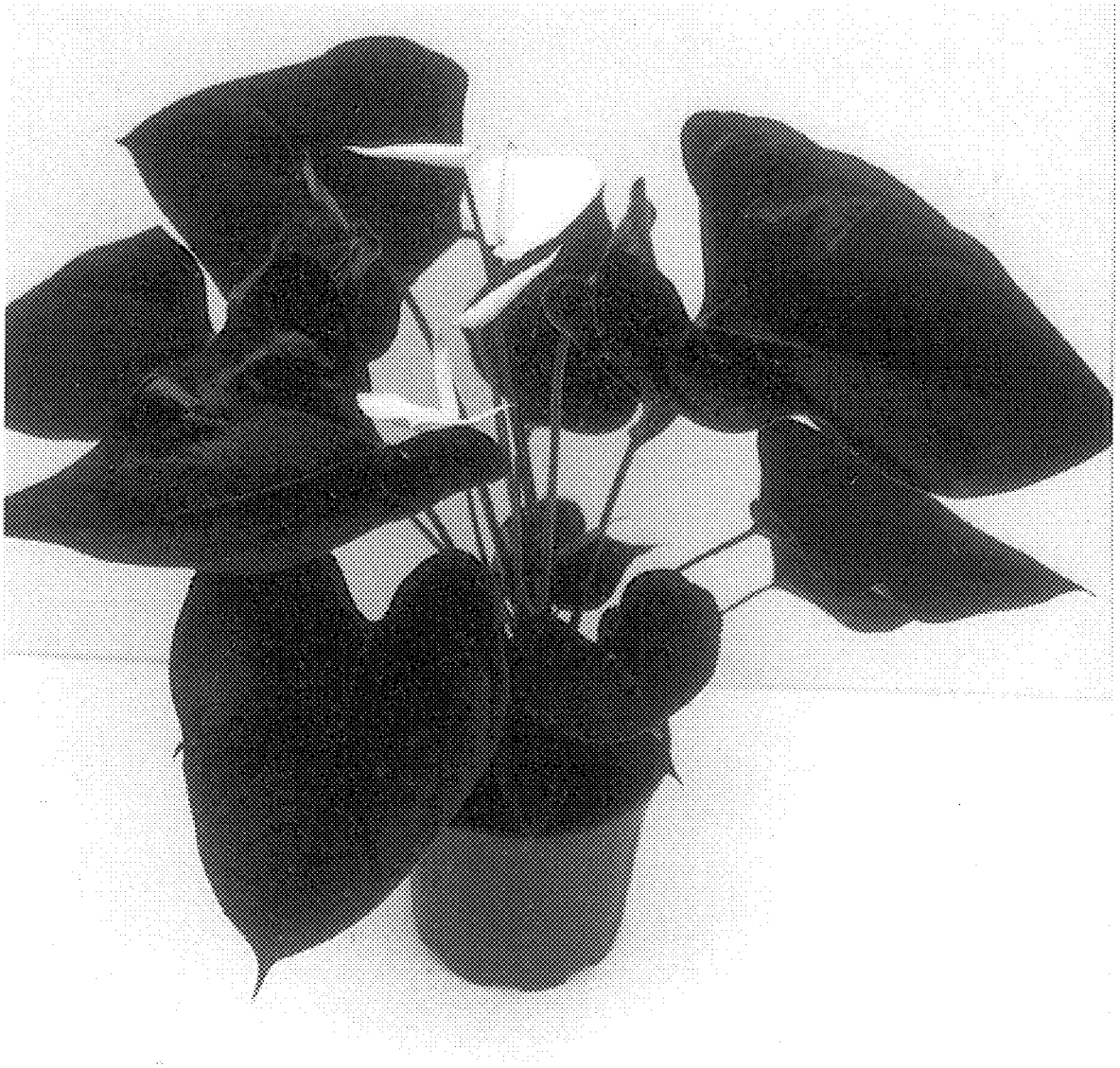

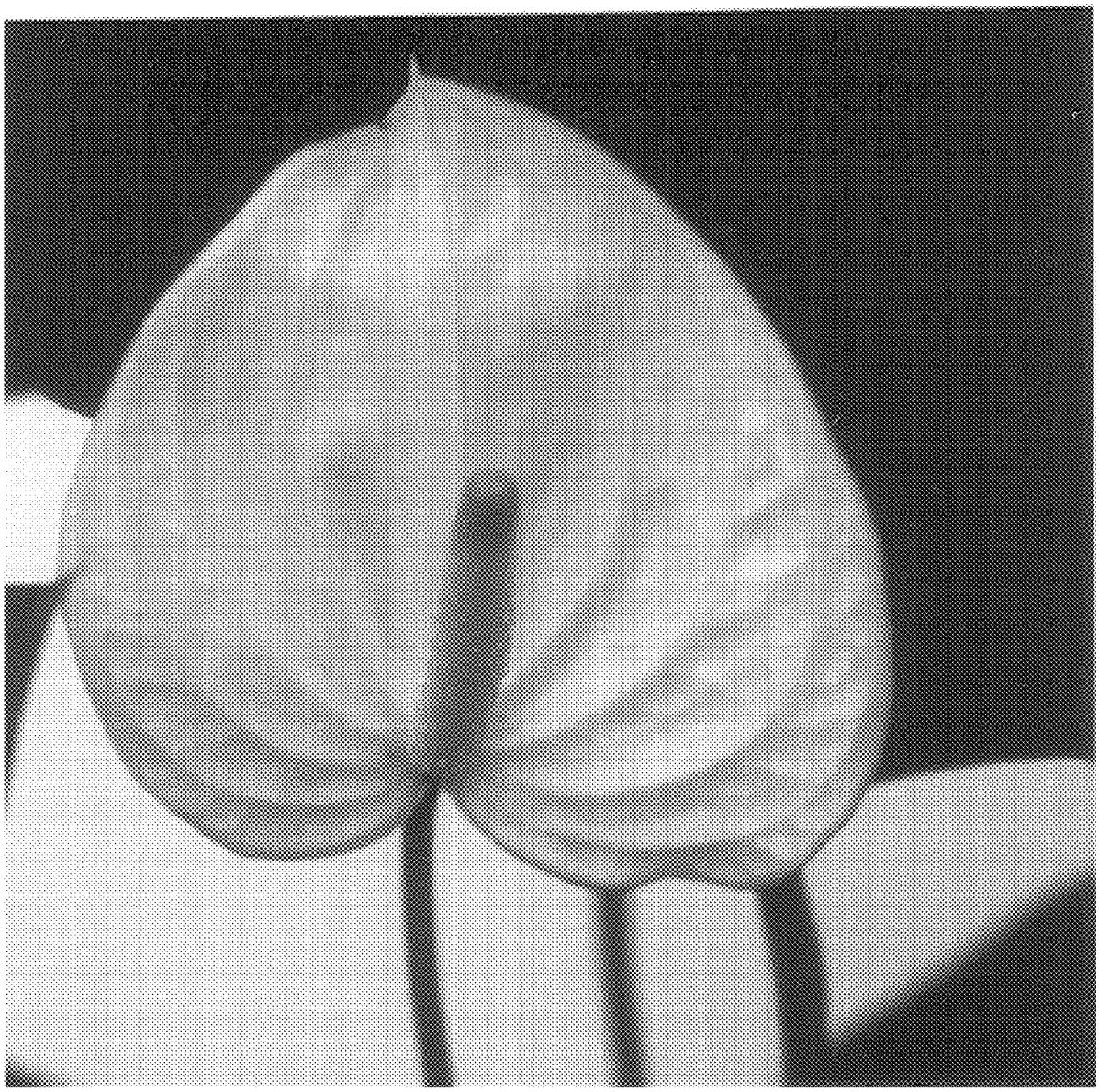

* * * * *